United States Patent [19]
Cubicciotti

[11] Patent Number: 5,656,739
[45] Date of Patent: Aug. 12, 1997

[54] NUCLEOTIDE-DIRECTED ASSEMBLY OF BIMOLECULAR AND MULTIMOLECULAR DRUGS AND DEVICES

[76] Inventor: Roger S. Cubicciotti, 258 Midland Ave., Montclair, N.J. 07042

[21] Appl. No.: 487,959

[22] Filed: Jun. 7, 1995

Related U.S. Application Data

[62] Division of Ser. No. 169,517, Dec. 17, 1993.

[51] Int. Cl.$^6$ .............. C07H 21/04; C12Q 1/68; C12Q 1/70; C19P 19/34
[52] U.S. Cl. .............. 536/23.1; 435/6; 435/5; 435/91.1; 536/24.3; 536/24.32; 536/24.33; 530/300; 530/388.1
[58] Field of Search .............. 435/6, 5, 91.1, 435/91.2, 7.1–7.9; 536/25.5, 34.3–33; 530/388.1, 300

[56] References Cited

U.S. PATENT DOCUMENTS

| | | | |
|---|---|---|---|
| 3,977,941 | 8/1976 | Vieth et al. | 195/63 |
| 4,203,802 | 5/1980 | Rubenstein et al. | |
| 4,601,981 | 7/1986 | Vieth et al. | 435/94 |
| 5,118,801 | 6/1992 | Lizardi et al. | 536/27 |
| 5,270,163 | 12/1993 | Gold et al. | 435/6 |
| 5,434,257 | 7/1995 | Matteucci et al. | 536/24.3 |
| 5,437,977 | 8/1995 | Segev | 435/6 |
| 5,527,690 | 6/1996 | Goldstein et al. | 435/69.1 |

FOREIGN PATENT DOCUMENTS

0491059A1  6/1992  European Pat. Off. .

OTHER PUBLICATIONS

Helene, Tibtech 9: 341–342 (Of Interest) 1991.

Hemat and McEntee, Biochemical And Biophysical Research Commun. 205: 475–481 (Of Interest) 1993.

Letsinger et al, J. Am. Chemical Society 115: 7535–7536 (Of Interest) 1993.

Franscesconi et al., Molecular And Cellular Biology 9: 2906–2913 1989.

Jalinot et al. PNAS 85: 2484–2488 (Of Interest) 1988.

Luche et al, PNAS 89: 7412–7416,(Of Interest) 1992.

Seeman Clin. Chem 39: 722 1993.

Seeman, N.C., "Branched DNA: A 3–D Structural Design System", Clin. Chem. 1993, 39: 722.

Heller et al., "Self–Organizing Molecular Photonic Transfer Structure Based on Chromophoric Oligonucleotide Derivatives", Clin. Chem., 1993, 39: 742.

Primary Examiner—W. Gary Jones
Assistant Examiner—Dianne Rees
Attorney, Agent, or Firm—Law Offices of Jane Massey Licata

[57] ABSTRACT

Methods of producing synthetic heteropolymers and multivalent heteropolymeric hybrid structures capable of assembling non-oligonucleotide molecules are provided. These structures are used to direct the assembly of multimolecular complexes. A number of synthetic heteropolymers, multivalent heteropolymeric hybrid structures and multimolecular complexes are also provided.

22 Claims, No Drawings

NUCLEOTIDE-DIRECTED ASSEMBLY OF BIMOLECULAR AND MULTIMOLECULAR DRUGS AND DEVICES

This is a divisional of application Ser. No. 08/169,517, filed Dec. 17, 1993.

BACKGROUND OF THE INVENTION

Biological systems perform intricate functions by sophisticated molecular organization of complex molecules such as enzymes, antibodies, transmitters, receptors and regulatory proteins. Such intricate functions include signal transduction, information processing, cellular replication, growth and differentiation, biosynthesis, detoxification and transduction of chemical energy into heat and work. Wound healing, blood coagulation, muscle contraction, hormone secretion and complement-mediated immunity, for example, all represent forms of biological functions that depend on multi-tiered cascades of biochemical reactions by organized molecules. Transport of ions and metabolites, gone expression and protein assembly represent a few of the many cellular functions that rely on concerted interaction of organized multiple biochemical systems. Efforts to simulate the productivity and efficiency of biomolecular machinery have been only marginally successful because of the inability to recreate the structural organization of molecules and groups of molecules inherent in highly ordered biological systems.

Biological systems have evolved two major capabilities that enable molecular manufacturing and nanomachinery far more sophisticated than chemical and biochemical methods developed by man. First, they have mastered the art of self-assembly, wherein discrete molecules either spontaneously organize or are chaperoned into supramolecular assemblies that perform complex functions through concerted interaction of the constituent molecules. Second, the rate and direction of biological reactions is manipulated through compartmentalization of reactants, catalysts and products, most commonly through physical segregation by cellular or subcellular membranes.

Efforts to develop self-assembling systems and microcompartmentalized biochemical reactions have escalated over the past several years. Historically, experimental approaches to self-assembly have been modeled after spontaneous association of lipids into monolayers and bilayer membranes. More recently, self-assembly has been attempted using lipid-protein mixtures, engineered proteins, branched DNA, and supramolecular chemistry.

Compartmentalization has been attempted through a wide range of approaches, including liposomes, microimmobilization techniques (e.g., photolithography) and targeted delivery (e.g., therapeutic immunoconjugates). Microscopic arrays of peptides and oligonucleotides have been achieved through light-directed combinatorial in situ synthesis on silicon substrates. However, the resolution of this technique is about a million-fold inadequate for ordered molecular arrays. Discrete resolution and manipulation of matter at the atomic level is being pursued through scanning tunneling microscopy and atomic force microscopy, but these techniques have not been developed for production-scale preparation of molecular arrays.

In a related area of bimolecular engineering, several types of bifunctional or hybrid molecules have been developed for diagnostic imaging and targeted drug delivery. Some of these include: chimeric antibodies, particularly humanized antibodies designed to eliminate human anti-mouse immune responses upon in vivo administration; bispecific antibodies produced through enzymatic digestion of parent antibodies and controlled reconstitution using Fab fragments obtained from two different parents; conventional immunoconjugates, composed of a drug, toxin or imaging agent covalently attached or chelated to an antibody or antibody fragment through established immunochemical methods; and fusion proteins, most commonly immunotoxins for cancer therapy, generated from hybrid genes developed and expressed through recombinant methods. While these hybrid molecules, especially fusion proteins, provide a practical approach to controlled production of hybrid gene products, none of the above methods provides a unified approach to directed multimolecular assembly.

Many methods have been described for site-directed attachment of effectors (e.g., enzymes, isotopes, drugs, fluorophores) to antibodies, antigens, haptens and nucleic acid probes. However, these methods represent bulk techniques that do not provide sufficient specificity for reproducible preparation of ordered molecular pairs, groups or arrays. Further, while these methods enable production of bifunctional conjugates, they do not provide for concerted interaction between the constituent moieties (e.g., probe and reporter molecules).

Branched DNA has been used as a carrier for accommodating large numbers of enzyme labels (e.g., alkaline phosphatase), thus enabling biochemical amplification of specific binding reactions in diagnostic assays. Scientists investigating branched DNA as a three-dimensional structural design system have speculated that natural mechanisms by which drugs and particular proteins recognize and bind to specific sites on DNA could be applied to attach molecular electronic components to DNA for development of memory devices (Seeman, N. C., *Clin. Chem.* 1993, 39, 722). Seeman has also suggested attaching conducting polymers, such as trans-polyacetylene or polyphenothiazine, a PTL-ruthenium switch and a redox bit into the branched DNA. However, they have not suggested using a single oligonucleotide or hybridized pairs of oligonucleotides for coordinated placement of two or more different molecules within a single DNA structure. They also have not suggested selecting or engineering nucleotides to achieve requisite affinity for molecules that have no natural mechanisms for recognizing specific sites on DNA.

Recognition and self-assembly are the two critical properties of chemical structures being explored in the rapidly advancing field of supramolecular chemistry. This field focuses on the designed chemistry of intermolecular bonds. For example, 12-crown-4-ether contains a central cavity that is highly specific for lithium. In fact, the components of this ring structure will self-assemble when exposed to a solution of lithium. Crown ethers and related structures are being investigated for their utility as highly selective sensors, sieves, synthetic enzymes and energy transfer structures for use in artificial photosynthesis. Other emerging applications include molecular switches, diodes, translators and molecular wires, and it has been proposed that supermolecule interactions on thin films may enable computers to be built around liquid-phase assembly reactions.

A general method has now been developed which provides for controlled placement of two or more selected molecules in appropriate spatial proximity to produce cooperative molecular assemblies. This method yields multimolecular complexes through use of self-assembling synthetic heteropolymers or multivalent heteropolymeric hybrid structures comprising nucleotides having defined sequence segments with affinities for identified molecules.

SUMMARY OF THE INVENTION

An object of the present invention is to provide a method of assembling non-oligonucleotide molecules or groups of molecules into bimolecular or multimolecular complexes.

Another object of the present invention is to provide a method of assembling multimolecular complexes that combine the functional activities of selected molecules with the capability of oligonucleotides to specifically hybridize to selected nucleic acid sequences, wherein the activity of the complexes can be modulated by the selected nucleic acids sequences.

Another object of the present invention is to provide a method of assembling multimolecular complexes that combine the functional activities of selected molecules with the capability to specifically bind other selected molecules, wherein the activity of the complexes can be modulated by the selected molecules.

Another object of the present invention is to a provide a synthetic heteropolymer of nucleotides having at least a first and a second defined sequence segment, wherein at least one of the defined sequence segments is capable of specifically binding to a non-oligonucleotide molecule or group of molecules.

Another object of the present invention is to provide a multivalent heteropolymeric hybrid structure made up of at least two synthetic heteropolymers, each synthetic heteropolymer comprising nucleotides having at least a first and second defined sequence segment. The first defined sequence segment of at least one synthetic heteropolymer is capable of specifically binding to a non-oligonucleotide molecule or group of molecules. The second defined sequence segments of each synthetic heteropolymer are capable of hybridization.

Another object of the present invention is to provide a multimolecular complex comprising one or more molecules specifically bound to a synthetic heteropolymer or a multivalent heteropolymeric hybrid structure.

Another object of the invention is to provide an immobilized reagent comprising a synthetic heteropolymer, multivalent heteropolymeric hybrid structure, or a multimolecular complex and a solid support, wherein the synthetic heteropolymer, multivalent heteropolymeric hybrid structure, or multimolecular complex is capable of attaching to the solid support.

DETAILED DESCRIPTION

This invention relates to methods and structures for coupling the activities of two or more molecules or groups of molecules, preferably molecules with defined activities, to perform functions dependent on the spatial proximity of constituent molecules. The present invention provides a method for assembling selected molecules into a single structure through use of synthetic heteropolymers or multivalent heteropolymeric hybrid structures comprised of hybridizably linked synthetic heteropolymers. Each synthetic heteropolymer comprises nucleotides having at least a first and a second defined sequence segment. One defined sequence segment of a synthetic heteropolymer or multivalent heteropolymeric hybrid structure is capable of specifically binding to a selected non-oligonucleotide molecule or group of molecules, preferably a receptor, ligand or effector molecule. The other defined sequence segments are capable of either specifically binding to a different non-oligonucleotide molecule or group of molecules or of hybridization.

The present invention represents a novel approach to assembling ordered pairs, groups and arrays of molecules that maximizes two important features of nucleotides, preferably groups of nucleotides comprising oligonucleotides. First, nucleotides, preferably groups of nucleotides comprising oligonucleotides, can be selected or engineered to recognize a wide range of molecular targets with high affinity. Second, nucleotides, preferably groups of nucleotides comprising oligonucleotides, can be synthesized with a defined sequence segment that enables reproducible combination of two monofunctional heteropolymers into a single, bifunctional hybrid referred to herein as multivalent heteropolymeric hybrid structure. These features provide the ability to reproducibly engineer the assembly of limitless combinations of biological and nonbiological molecules with substantial control over both the design and production of desired complexes. The advantage of this approach over prior efforts to coax lipids and proteins into self-assembly is control over the assembly process. The present invention teaches methods to engineer defined sequence segments into a sequence of nucleotides, modified nucleotides or nucleotide analogs that control the proximity of two or more selected molecules by the relative positions of defined sequence segments along the sequence.

In the present invention, the term "synthetic heteropolymer" refers to nucleotides having at least two defined sequence segments wherein at least one defined sequence segment per discrete structure is capable of specifically binding a selected non-oligonucleotide molecule or group of molecules. The second defined sequence is capable of either specifically binding a different, selected non-oligonucleotide molecule or of hybridization.

The term "nucleotide" includes nucleotides and nucleotide analogs, preferably groups of nucleotides comprising oligonucleotides, and refers to any compound containing a heterocyclic compound bound to a phosphorylated sugar by an N-glycosyl link. The term "nucleotide analog" includes, but is not limited to, modified purines and pyrimidines, structural analogs of purines and pyrimidines, and nucleotides with backbone modifications, including, but not limited to, ribose-modified nucleotides, phosphoramidates, phosphorothioates, methylphosphonates, methylenephosphonates, phosphorodithioates, peptide nucleic acids, achiral and neutral internucleotidic linkages and non-nucleotide bridges such as polyethylene glycol, aromatic polyamides and lipids.

The term "discrete structure" refers to any single molecule or to any group of molecules bound to one another either covalently or through noncovalent interactions. Discrete structures of the present invention include synthetic heteropolymers, multivalent heteropolymeric hybrid structures comprising two or more hybridized synthetic heteropolymers, and multimolecular complexes comprising non-oligonucleotide molecules specifically bound to synthetic heteropolymers or multivalent heteropolymeric hybrid structures.

The term "defined sequence segment" refers to a selected or designed sequence of monomers, preferably a sequence of nucleotides, which is capable of specifically binding to an identified molecule or group of molecules or hybridizing to a selected nucleic acid sequence. "Hybridizing" refers to specific binding between two selected nucleic acid sequences through complementary base pairing. Such bonding is also referred to as Watson-Crick base pairing. For hybridization, a sufficient degree of complementarity is required such that stable binding occurs between two selected nucleic acid sequences. However, perfect complementarity is not required.

"Selected molecules" or "identified molecules" include, but are not limited to, receptors, ligands and effector molecules which may exist as single molecules or groups of molecules. "Receptors" include, but are not limited to, membrane receptors, hormone receptors, drug receptors, transmitter receptors, autacoid receptors, antibodies, antibody fragments, engineered antibodies, antibody mimics, molecular recognition units, adhesion molecules, agglutinins, avidin and streptavidin. "Ligands" include, but are not limited to, receptor agonist, partial agonists, mixed agonists, antagonists, drugs, hormones, transmitters, autacoids, growth factors, cytokines, prosthetic groups, coenzymes, cofactors, regulatory factors, antigens, haptens, biotin and conjugates formed by attaching any of these molecules to a second molecule. "Effector molecules," also referred to as "molecular effectors" include, but are not limited to, enzymes, synthetic enzymes, catalytic antibodies, catalysts, contractile proteins, transport proteins, regulatory proteins, cytochromes, electroactive compounds, photoactive compounds, supermolecules and shape-memory structures. "Selected nucleic acid sequences" include, but are not limited to, defined sequence segments of other heteropolymers, oligonucleotides, and RNA or denatured DNA sequences.

The term "specifically binding" refers to a measurable and reproducible degree of attraction between a defined sequence segment and a particular molecule or selected nucleic acid sequence. The degree of attraction need not be maximized to be optimal. Weak, moderate or strong attractions may be useful in appropriate applications. The specific binding which occurs in these interactions is well known to those skilled in the art.

The synthetic heteropolymer of the present invention allows for the production of ordered pairs, groups and arrays of selected non-oligonucleotide molecules, preferably receptors, ligands or effector molecules, whose cooperative interactions have utility in diagnostics, therapeutics, bioprocessing, energy transduction and, more generally, molecular manufacturing. The terms "cooperating," "cooperative interactions" and "cooperativity" refer either to the ability of the identified molecules to interact positively or negatively to produce a desired result or refers to an effect on one molecule created by the presence of a second molecule. This invention enables preparation of ordered pairs, groups or arrays of selected biological or nonbiological molecules that function in a concerted manner to transduce energy or perform useful work. Whereas biological systems rely on membranes, and molecular chaperons and self-assembling systems to create ordered arrangements of proteins, lipids and glycoconjugates as ion channels, effector-coupled membrane receptors, biochemical amplifiers and metabolic pathways, the present invention teaches methods to create molecular machines using engineered nucleotides as ordering devices.

Bifunctional synthetic heteropolymers of the present invention are prepared in the following manner. Two molecules or groups of molecules capable of performing a useful function when brought into close spatial proximity are identified. At least one of the identified molecules is a non-oligonucleotide molecule, preferably a receptor, ligand or molecular effector. A first defined sequence segment capable of specifically binding to an identified non-oligonucleotide molecule is selected, preferably by repeated selection and amplification of oligonucleotide pools, more preferably by combinatorial selection and amplification of an oligonucleotide library. A second defined sequence segment capable of specifically binding to the second identified molecule, which may be a non-oligonucleotide molecule or a selected nucleic acid sequence, is also selected. A synthetic heteropolymer comprising the first and second defined sequence segments separated by a spacer sequence of variable length and composition, preferably about 1 to 40 nucleotides, is then synthesized ab initio by methods well known in the art. The length and composition of the spacer sequence is such that the spatial relationship between the first and second defined sequence segments is optimal to provide for specific binding of the two identified molecules in close intermolecular proximity. The three-dimensional shape of the synthetic heteropolymer and rigidity of the spacer sequence may be further modified by hybridizing one or more nucleotide sequences to the spacer sequence. In the instant application, the term "multimolecular complex" refers to synthetic heteropolymers or multivalent heteropolymeric hybrid structures having one or more identified molecules specifically bound to the synthetic heteropolymers.

Bifunctional or multifunctional hybrids of synthetic heteropolymers, referred to as multivalent heteropolymeric hybrid structures can be formed in accordance with the methods of the invention, having the ability to specifically bind two or more selected molecules or nucleic acid sequences.

The term "multivalent heteropolymeric hybrid structure" refers to two or more synthetic heteropolymers hybridizably linked. Each heteropolymer comprises nucleotides, preferably oligonucleotides, having at least two defined sequence segments. A first defined sequence segment of at least one heteropolymer is capable of specifically binding to a non-oligonucleotide molecule or group of molecules, preferably a receptor, ligand or molecular effector. Second defined sequence segments of the heteropolymers are capable of hybridizing to each other or to a linker oligonucleotide. The term "linker oligonucleotide" refers to an oligonucleotide sequence capable of hybridizing to a second defined sequence segment of two or more synthetic heteropolymers, thus joining the synthetic heteropolymers. Examples of the linker oligonucleotide include, but are not limited to: an oligonucleotide; a duplex, triplex or quadraplex structure having single stranded ends capable of hybridizing to the second defined sequence segments; a branched-chain structure having defined sequence segments capable of hybridizing to the second defined sequence segments; and a circular structure having defined sequences capable of hybridizing to the second defined sequence segments.

Bifunctional or multifunctional hybrids of synthetic heteropolymers, referred to as "multivalent heteropolymeric hybrid structures," may also be formed in accordance with the methods of the invention, having the ability to specifically bind two or more selected molecules or nucleic acid sequences. Two molecules or groups of molecules capable of performing a useful function when brought into close spatial proximity are identified, at least one of which is a non-oligonucleotide molecule, preferably a receptor, ligand or molecular effector. A first defined sequence segment capable of specifically binding to an identified non-oligonucleotide molecule is selected, preferably by repeated selection and amplification of oligonucleotide pools, more preferably by combinatorial selection and amplification of an oligonucleotide library. A first synthetic heteropolymer comprising the first defined sequence segment and a second defined sequence segment capable of hybridizing to a selected nucleic acid sequence is synthesized by methods well known in the art. A second synthetic heteropolymer comprising a first defined sequence segment selected to bind the second identified molecule and a second defined sequence segment capable of hybridizing with the second defined sequence segment of the first synthetic heteropolymer is synthesized by methods well known in the art. The first and second synthetic heteropolymers are then hybridized through their complementary second defined sequence segments to produce a multivalent heteropolymeric hybrid structure. The hybridized second defined sequence segments are of such length, preferably about 5 to 40 nucleotides and more preferably about 8 to 20 nucleotides, to provide for controlled spacing between the two defined sequence segments of the heteropolymeric hybrid structure that are capable of specifically binding to the identified molecules. Accordingly, these two defined sequence segments are separated by such distance, preferably 2 to 15 nm, to accommodate specific binding of the two identified molecules in close intermolecular proximity. The molecules can then be bound to their respective defined sequence segments of the heteropolymeric hybrid structure to form a multimolecular complex with specifically bound molecules suitably positioned for optimal function.

In accordance with a preferred embodiment of the present invention, two or more non-oligonucleotide molecules or groups of molecules capable of cooperating to carry out a desired function or functions, preferably receptors, ligands or molecular effectors, are assembled in a multimolecular complex in the following manner. Non-oligonucleotide molecules or groups of molecules capable of cooperating to carry out a desired function or functions are identified. A first defined sequence segment capable of specifically binding a molecule is selected for each molecule, preferably by repeated selection and amplification of oligonucleotide pools, more preferably by combinatorial selection of an oligonucleotide library. A synthetic heteropolymer or multivalent heteropolymeric hybrid structure comprising each of the first defined sequence segments is then prepared such that the arrangement and spacing of these defined sequence segments provides for specific binding of the identified molecules in close, spatially ordered intermolecular proximity. The identified molecules can then be specifically bound to their respective defined sequence segments to form a multimolecular complex capable of performing the desired cooperative function or functions of the constituent non-oligonucleotide molecules.

In addition, a synthetic heteropolymer, multivalent heteropolymeric hybrid structure or multimolecular complex capable of specifically binding to a selected nucleic acid sequence may be prepared by a modification of the above method, wherein a particular defined sequence segment is selected for its ability to hybridize to a selected nucleic acid sequence. A synthetic heteropolymer capable of specifically binding to a selected nucleic acid sequence may be prepared by selecting a second defined sequence segment capable of hybridization, preferably a nucleic acid probe sequence. A heteropolymeric hybrid structure capable of specifically binding to a selected nucleic acid sequence may be prepared by selecting a first defined sequence segment of a constituent synthetic heteropolymer capable of hybridization, preferably a nucleic acid probe sequence. A multimolecular complex capable of specifically binding to a selected nucleic acid sequence may be prepared by specifically binding selected molecules to either a synthetic heteropolymer or a heteropolymeric hybrid structure comprising a suitable defined sequence segment capable of hybridization.

The synthetic heteropolymers, multivalent heteropolymeric hybrid structures and multimolecular complexes of the present invention can be added to a reaction mixture directly, incorporated into a device, or they may be capable of attaching to solid supports and matrices including, but not limited to, thin and thick films, lipid bilayers, microvessicles, membranes, organic polymers, microparticles, and inorganic substrates such as silicon, silica, plastics, polymers, graphite and metals. They may be immobilized or conjugated by covalent attachment, hybridization, adsorption or controlled deposition. immobilization may also be achieved by in situ synthesis of constituent synthetic heteropolymers or oligonucleotide linkers on suitable substrates followed by in situ self-assembly of heteropolymeric hybrid structures or multimolecular complexes.

The proximity of the selected defined sequence segments to one another within the synthetic heteropolymer or multivalent heteropolymeric hybrid structure, which is controlled by the length of the spacer nucleotide and linker oligonucleotide sequences is such that the binding of a molecule at one defined sequence segment can modulate the affinity of another defined sequence segment for a second non-oligonucleotide molecule. Modulating the affinity refers to any increase or decrease in the association or dissociation rate constants that characterize the binding between a defined sequence segment and its specific binding partner. The binding of a molecule at one defined sequence segment can also modulate the activity of a molecule bound to another defined sequence segment. Modulating the activity refers to restoration or elimination in part or in full of the biological, chemical, optical or electrochemical activity of a selected molecule. For example, in a diagnostic assay, specific binding of a non-oligonucleotide molecule such as a receptor or ligand to a second defined sequence segment of a synthetic heteropolymer may decrease the binding affinity of a first defined sequence segment for a bound, inactive or partially inactive molecular effector. This results in displacement of the molecular effector and restoration of its activity. Thus, the presence of the selected receptor or ligand may be monitored by measuring activity of the molecular effector.

The activity of a molecule specifically bound at one defined sequence segment can also modulate the affinity of a second defined sequence segment for a second non-oligonucleotide molecule. Local production of hydrogen ions by an enzyme specifically bound to one defined sequence segment, for example, can modulate the affinity of a second defined sequence segment for a second molecule by decreasing the microenvironmental pH surrounding the second defined sequence segment. Similarly, the activity of a non-oligonucleotide molecule specifically bound at one defined sequence segment can modulate the activity of a second molecule bound to a second defined sequence segment. A specifically bound enzyme, for example, may generate any number of products, including hydrogen ions, electrons, photons, heat, substrates, prosthetic groups, cofactors or inhibitors, that can influence the activity of a second bound effector either directly or through effects on the microenvironment. The occupation state of a ligand or receptor bound at one defined sequence segment can also modulate the affinity of a second defined sequence segment for a second non-oligonucleotide molecule or the activity of the second non-oligonucleotide molecule. Specific binding of a ligand bound at one defined sequence segment to its receptor, for example, can increase the dissociation rate of a selected second molecule bound to a second defined sequence segment through steric or conformational effects. The activity of the second molecule can increase or decrease with dissociation, depending on its relative activity in the bound and free states.

The synthetic heteropolymers, multivalent heteropolymeric hybrid structures and multimolecular complexes of the present invention may be used in a variety of applications which will become apparent to those skilled in the art upon reading this disclosure. The present invention may serve as a homogenous nucleic acid probe diagnostic used to report hybridization reactions. Nucleic acid probes are single-stranded sequences of DNA or RNA that specifically hybridize to defined target sequences of nucleic acids in a test sample. DNA probes, labeled with a detectable marker such as an enzyme, isotope, fluorophore or chemiluminescent compound, provide a useful means for detecting and quantifying selected nucleic acid sequences in biological samples. DNA probe diagnostics have yet to realize substantial commercial success, however, largely because the complexity of test protocols have precluded routine implementation in clinical laboratory settings. In addition, current DNA probe assays are substantially more time-, labor-, skill- and cost-intensive than the two major in vitro diagnostic modalities, clinical chemistry and immunodiagnostics.

In general, present technologies for heterogeneous DNA probe diagnostics involve the following steps. Genomic or plasmid DNA is extracted from test samples. The DNA is denatured to prepare single stranded targets. Target sequences are then amplified by successive replication using methods such as the polymerase chain reaction (PCR) or ligase chain reaction (LCR). Amplified target sequences are immobilized, and labeled probes are hybridized to the immobilized targets. The immobilized probe-target hybrids then require separation from unbound probes and successive washing before the bound probes can be detected by addition of a signal generator.

In accordance with the present invention, a variety of homogenous DNA probe reagents can be prepared utilizing synthetic heteropolymers which simplify this process. In the present invention, the term "homogeneous," as contrasted with "heterogeneous" refers to properties of assay reagents that eliminate the need for tedious separation and washing steps. In homogeneous assays, the activity of a detectable label is altered when a probe specifically binds its target. Specific binding can then be quantified without physically separating bound complexes from unbound reagents. In one embodiment, a multimolecular complex comprises a synthetic heteropolymer having an effector molecule specifically bound to one of the defined sequence segments. Examples of preferred molecular effectors include, but are not limited to, such detectable species as chromogenic, fluorescent, chemiluminescent, bioluminescent, electroactive compounds and enzymes, more preferred enzymes being glucose-6-phosphate dehydrogenase (G6PDH), acetyl cholinesterase, glucose oxidase, β-galactosidase, lysozyme and malate dehydrogenase. The second defined sequence segment of the multimolecular complex is capable of hybridizing with a selected nucleic acid sequence. This defined sequence segment serves as a nucleic acid probe. The multimolecular complex may be incorporated into a dry-reagent test device, attached to a solid support to create an immobilized reagent or added to a liquid reaction mixture. In this embodiment, the activity of the molecular effector is modulated by target hybridization at the second defined sequence segment. It will be appreciated by those skilled in the art that many permutations of a single-reagent homogeneous format can be developed by selecting different combinations of molecular effectors and defined sequence segments. The state of activity of a particular molecular effector depends on the binding locus, length and affinity of the selected defined sequence segment, which can be optimized for maximal target-dependent modulation.

In another embodiment, the multimolecular complexes of the present invention comprise a synthetic heteropolymer having a ligand specifically bound to a first defined sequence segment and a second defined sequence segment capable of hybridization. The multimolecular complex may be attached to a solid support to create an immobilized reagent, incorporated into a dry reagent test device, or added to a liquid reaction mixture. In this embodiment, hybridization at the second defined sequence segment can modulate either the affinity of the first defined sequence segment for the ligand or the activity of the ligand, resulting in activation or inhibition of a molecular effector that is not a constituent of the multimolecular complex.

This same basic reagent composition described for homogeneous DNA probe diagnostics can be used for pseudo-immunodiagnostic applications through modular substitution of the defined sequence segments. Homogeneous diagnostic assays employing molecular effector-oligonucleotide complexes to detect non-oligonucleotide molecules represent a replacement technology for immunodiagnostics. The utility of this approach resides in its simplicity, ease of use, modular design and versatility. By selecting defined sequence segments that specifically bind to non-oligonucleotide molecules which are to be analyzed, hereinafter analytes, diagnostic reagents can be developed which function much like labeled antibodies but with a number of important advantages. Activation of a molecular effector, preferably an enzyme, bound at a first defined sequence segment by analyte binding at the second defined sequence segment provides for a homogenous, single-step, single-reagent diagnostic test. In addition, labeling of the synthetic heteropolymer with the molecular effector is accomplished by self-assembly of specific binding partners, thereby precluding tedious and imprecise covalent conjugations.

Development of new diagnostic products using the modular design approach requires only selection and optimization of one defined sequence segment of the synthetic heteropolymer. The defined sequence segment that binds the molecular effector, the molecular effector itself, and any linker oligonucleotides are conserved from product to product. This modular approach to product development is both efficient and economical. Unlike homogeneous immunoassays, which tend to be best suited for either large molecules or small molecules, the present approach provides a common reagent configuration and assay protocol for any class of analytes. These pseudo-immunodiagnostic compositions can be incorporated into any reagent delivery system including, but not limited to, slides, cartridges, sensors, test tubes, microtiter plates and autoanalyzer reagent channels.

In one embodiment of homogeneous pseudo-immunodiagnostics, low molecular weight analytes are detected with high sensitivity in the following manner. A multimolecular complex is prepared comprising a synthetic heteropolymer or multivalent heteropolymeric hybrid structure with a reporter molecule, preferably a molecular effector, more preferably, an enzyme such as G6PDH, specifically bound to one defined sequence segment and the ligand moiety of a ligand-carried conjugate specifically bound to a second defined sequence segment. Examples of analytes for which such a complex is useful include, but are not limited to, hormones such as thyroxine ($T_4$) and triiodothyronine ($T_3$), prolactin, cortisol, estriol, estradiol, progesterone and testosterone; therapeutic drugs such as theophylline, digoxin, phenytoin, valproic acid, phenobarbital, antibiotics and immunosuppressants; and drugs of abuse such as THC, cocaine, PCP, opiates and amphetamines. Due to their low molecular weight, some of these analytes may not be as effective in modulating the activity of a molecular effector specifically bound to a synthetic heteropolymer as a high molecular weight analyte such as a protein, immunoglobulin or cell surface antigen. The impact of specific binding of such low molecular weight analytes to a first defined sequence segment of a multimolecular complex on the activity or affinity of an effector molecule specifically bound to a second defined sequence segment can be amplified through analyte-dependent displacement of a large ligand-carrier conjugate from the first defined sequence segment.

The homogeneous configurations of the present invention can be adapted for use with a wide range of reporter molecules. Examples of molecular effectors that can serve as effective reporters in a multimolecular complex include, but are not limited to, fluorophores, phosphors, bioluminescent and chemiluminescent reagents, quenchable dyes, activatable dyes and enzyme-enhanced luminescent and fluorescent reagent systems. Homogeneous pseudo-immunodiagnostic configurations are therefore compatible with all existing and anticipated nonisotopic detection systems, including, but not limited to, spectrophotometers, reflectance photometers, luminometers, fluorimeters, potentiostats, potentiometers, and confocal and fluorescent microscopes.

Classes of analytes for which multimolecular pseudo-immunodiagnostic complexes may be most useful include, but are not limited to: infectious diseases, including viral, bacterial and fungal antigens and antibodies against these antigens; endocrinology and metabolism, including thyroid and reproductive hormones, $B_{12}$, folate, ferritin, glycosylated hemoglobin, parathyroid hormone calcitonin and cortisol; therapeutic drugs, including theophylline, digoxin, phenytoin, valproic acid, phenobarbital, antibiotics and immunosuppressants; allergy and immunology, including allergen-specific IgE and autoantibodies; drugs of abuse, including cocaine, cannabinoids, phencyclidine and amphetamines; cancer, including CEA, AFP, CA 125, CA 50, CA 19-9, CA 15-3, PAP and PSA; and cardiovascular disease, including apolipoproteins, fibrinogen, cardiac enzymes and isoforms, troponin, myosin light chains and myoglobin.

Clinical chemistry tests relying on coupled enzyme reactions can also be performed efficiently and with high sensitivity through use of multimolecular complexes. The benefits of using multimolecular complexes over conventional reaction mixtures include increased sensitivity, reagent stability and reaction rates; decreased sample volume and reagent mass/test; and suitability for direct signal transduction using immobilized multimolecular complexes.

An in vitro diagnostic tool is just one of the many applications for synthetic heteropolymers, multivalent heteropolymeric hybrid structures and multimolecular complexes. Molecular complexes comprising multiple coupled effector molecules, such as enzymes, represent "molecular processing" compositions that can be applied to cost-effective biosynthesis, including the production of chiral drugs and intermediates, industrial production and processing, computer-aided metabolic simulation and development of artificial organs. The multimolecular complexes described for homogenous diagnostic assays are special examples of stimulus-sensitive molecular effectors or "molecular switches" that can be applied to in vivo diagnostic imaging, implantable devices, biosensors and biochips, pharmaceuticals and drug delivery.

The combination of homogeneous DNA probes, homogeneous pseudo-immunodiagnostic assays and coupled enzyme clinical chemistries provides a unified approach to the three major classes of in vitro diagnostics, thereby enabling development of a universal clinical analyzer through use of multimolecular complexes.

For example, using a therapeutic enzyme as the molecular effector component of a multimolecular complex, delivery of the active therapeutic can be triggered by a specific binding event between an unoccupied defined sequence segment of the complex and a physiological receptor or pathological target. Examples of therapeutic enzymes include, but are not limited to, tissue plasminogen activase and streptokinase (for acute myocardial infarction and pulmonary embolism), superoxide dismutase (for oxygen toxicity in premature infants), DNase (for cystic fibrosis, chronic bronchitis) and ceredase (for Gaucher's disease). It will be appreciated by those skilled in the art that in addition to enzymes, a virtually limitless array of therapeutic effectors can be specifically bound in inactive or inaccessible form to one defined sequence segment of a synthetic heteropolymer of multivalent heteropolymeric hybrid structure such that activation occurs upon specific binding of a second defined sequence segment to a physiological receptor or pathological target.

Many diseases, syndromes and pathological processes are multifactorial, suggesting the potential clinical value of combination therapies. However, combination therapies present significant risks in the form of combined toxicities and drug interactions. Major therapeutic development strategies aimed at increasing drug efficacy without concomitant increases in toxicity revolve around novel drug delivery and targeting approaches. Therapeutic immunoconjugates for site-specific delivery of radioisotopes or cytotoxins have received a great deal of attention over the past decade. Fusion proteins comprising a targeting moiety and a toxic moiety are also being developed for infectious diseases and cancer.

Synthetic heteropolymers, multivalent heteropolymeric hybrid structures and multimolecular complexes enable novel approaches to combination therapies and targeted drug delivery that cannot be achieved using therapeutic immunoconjugates or fusion proteins. In simplest form, synthetic heteropolymers or multivalent heteropolymeric hybrid structures can be designed to specifically bind two or more neighboring sites on a single pathophysiological target. Bifunctional heteropolymers, for example, can act upon: two sites on a single molecule, such as an enzyme and a receptor; two molecules in a single structure, such as two proteins in a multimolecular receptor-effector system or a vital protein and nucleic acid sequence; or two molecules on different structures, such as cell adhesion molecules or receptors located on different cells. Although most of these approaches are technically plausible with immunoconjugates, bispecific antibodies or fusion proteins, synthetic heteropolymers and multivalent heteropolymeric hybrid structures provide a number of advantages that render them substantially more useful. First, nucleotide sequences that make up the synthetic heteropolymers can be selected and synthesized with desired specificity and affinity for either specific nucleic acid sequences or non-oligonucleotide molecules. Second, unlike bispecific antibodies and therapeutic immunoconjugates, heteropolymeric hybrid structures can be conveniently engineered with three or more specific binding sequences. Third, synthetic heteropolymers and multivalent heteropolymeric hybrid structures can be synthesized by established chemical methods, obviating the technical challenges and uncertain outcomes of designer antibody and fusion protein production. Fourth, the spacing of multiple specific binding sequences in synthetic heteropolymeric and multivalent heteropolymeric hybrid structures can be rationally designed and controlled through systematic production and evaluation of structures composed of variable-length spaces sequences and oligonucleotide linkers. In addition to two-site therapeutic actions, a number of other drug development approaches can be pursued through nucleotide-directed molecular assembly.

In a first embodiment, multimolecular complexes are synthesized comprising two or more specific binding sequences, wherein a therapeutic drug is specifically bound to a first defined sequence segment and the second defined sequence segment is capable of specifically binding to a therapeutic target. This embodiment enables use of the specifically bound drug as a targeting agent for site-specific delivery of the unoccupied specific binding sequence or, alternatively, use of the unoccupied defined sequence segment for site-specific delivery of the bound drug. In either case, the combination of drug action and specific binding of the unoccupied defined sequence segment to a pathophysiologic target can produce therapeutic effects through two distinct mechanisms of action. For example, a therapeutic for HIV comprising a multimolecular complex having a protease or reverse transcriptase inhibitor specifically bound to one site of a synthetic heteropolymer with an HIV-specific DNA probe or antisense sequence as the second site.

In a second embodiment, combination therapies relying on multimolecular complexes comprising a ligand, preferably a therapeutic drug, specifically bound to one defined sequence segment and a molecular effector, preferably an enzyme, specifically bound to a second defined sequence segment are synthesized. In this embodiment, a high-affinity ligand may be used to deliver the complex to a particular site where simultaneous actions of the ligand and the molecular effector yield an additive or synergistic therapeutic effect. An example of such a multimolecular complex is an adenosine regulating agent such as Arasine™ (Gensia Pharmaceuticals, San Diego, Calif.) specifically bound to a first defined sequence segment with the enzyme tissue plasminogen activase or Activase™ (Genentech, San Francisco, Calif.) bound to a second defined sequence segment to yield localized thrombolytic and cardioprotective effects in perimyocardial infarction, coronary artery bypass surgery and angioplasty procedures.

In a third embodiment, combination therapies relying on multimolecular complexes comprising different ligands, preferably drugs, specifically bound to different defined sequence segments of a synthetic heteropolymer or multivalent heteropolymeric hybrid structure are synthesized. Examples of pairs of ligands which can be bound to selected defined sequence segments of heteropolymeric hybrid structures include, but are not limited to: a histamine $H_2$ receptor antagonist such as Tagamet™ (SmithKline Beecham Pharmaceuticals, King of Prussia, Pa.) and a proton pump inhibitor such as Losec™ (Astra AB Pharmaceuticals, Sodertalje, Sweden) for the treatment of gastric ulcers; a histamine $H_1$ receptor antagonist such as terfenadine and a mast cell release inhibitor such as cromolyn sodium for the treatment of histamine-mediated diseases such as bronchial asthma; an interleukin such as IL-3 and a colony stimulating factor such as GM-CSF for treatment of leukemias, cerebral malaria, leishmaniasis and allergic disorders such a bronchial asthma; and a P-glycoprotein inhibitor such as verapamil or cyclosporin and one or more chemotherapeutic agents such as 5-FU and levamisole to eliminate the risks of multi-drug resistance while treating malignancies.

It is preferred that the combination therapies discussed be administered in a triggered release configuration, wherein binding of a first defined sequence segment, as in the first embodiment, or specifically bound ligand, as in the second or third embodiment, to its therapeutic receptor releases or activates the ligand or effector specifically bound to a second defined sequence segment of a multimolecular complex. For example, binding of the $H_2$ antagonist Tagamet™ to a gastric histamine receptor would result in release of Losec™ to the gastric proton pump through a conformational shift in the multivalent heteropolymeric hybrid structure used to deliver the two drugs.

In addition to the diagnostic and therapeutic utilities discussed, the present invention can also be utilized in a variety of applications including, but not limited to: sequential, multistep enzymatic synthesis of a particular product or degradation or a toxic metabolite; coupling proteins to selectively or actively transport ions and metabolites; coupling cytochromes to transduce chemical energy by means of electron transfer-dependent oxidation-reduction reactions; coupling redox mediators such as ubiquinones, ferricinium salts, rubidium, viologens, tetrathiofulvalene, tetracyanoquinidodimethane, N-methylphenazinium, benzoquinone or conducting polymers or organic conducting salts to transfer electrons between electroactive molecules such as redox enzymes and electrodes in bioelectronic and optoelectronic devices such as biosensors and biochips; coupling photoactive compounds such as fluorophores with other photoactive compounds or with redox proteins or enzymes for energy transfer devices and artificial photosynthetic systems; and coupling pro-drugs for staged-delivery or triggered activation. Medical applications that rely on ordered arrangements of one or more exogenously administered molecules with an endogenous pathophysiological target include, but are not limited to: targeting radioconjugates or radiochelates of gamma-emitting isotopes such as iodine-131, iodine 123, indium-111, technetium-99m and copper-67 to pathophysiological markers such as cancer antigens CEA, TAG-72, CA 125 and CA 19-9 for in vivo diagnostic imaging; targeting radioconjugates, cytotoxins or cytotoxic cells to disease markers for localized cell kill; and targeting drugs to pathophysiologic receptors to achieve receptor-, cell- or tissue-selective therapeutic action.

Nucleotide-directed enzyme assembly using multimolecular complexes provides a general method for production of spatially ordered, cooperative multienzyme systems. Applications include, but are not limited to, production of chiral intermediates and chiral drugs, industrial biosynthesis and bioprocessing, diagnostics, detoxification and computer-aided metabolic simulation. Advantages over soluble multienzyme systems include control over the spatial arrangement of individual enzymes within complexes; control over protein-protein interactions, diffusion distances and diffusion times; direct channeling of the product of one enzyme to a proximate enzyme; increased efficiencies through preferential reaction with the Nernst layer; protection of unstable intermediates; regulation of microenvironmental factors; control over the direction of thermodynamically unfavorable reactions; and enhanced enzyme stability. Of particular commercial value, nucleotide-directed enzymatic cycling can be used to drive NAD(P)H- and ATP-driven biosynthetic reactions using catalytic amounts of expensive pyridine nucleotides. In addition, multistep sequential reactions involving unstable intermediates can be efficiently coordinated through nucleotide-directed juxtaposition of participating enzymes.

Sequential, multistep enzymatic synthesis refers to the conversion of an initial substrate into a final product through a series of enzyme reactions, wherein each proximal enzyme generates a product that is a substrate for a subsequent enzyme reaction. Practical application of multistep enzyme systems to industrial scale production requires enzymatic cycling. This technique has been developed for soluble enzymes and has stimulated intense efforts in the area of immobilized enzyme systems. For purposes of this invention, "enzymatic cycling" refers to the shuttling of oxidized and reduced forms of a coenzyme between two linked enzymes. This type of reaction scheme is useful for a variety of applications. There are over 250 NADH-dependent dehydrogenases alone, not including NAD(P)H-dependent enzymes. Representative NADH-dependent dehydrogenases currently used in clinical, fermentation, food and environmental applications include, but are not limited to, alcohol dehydrogenase, 3α-hydroxysteroid dehydrogenase, lactate dehydrogenase, malate dehydrogenase, glutamate dehydrogenase, glucose dehydrogenase, amino acid dehydrogenase, tartrate dehydrogenase, 12α-hydroxysteroid dehydrogenase, estradiol 17α-dehydrogenase, aryl-alcohol dehydrogenase and testosterone β-dehydrogenase.

Extremely sensitive determination of either NAD(P)H or analytes can be achieved through enzymatic cycling. Concentrations of NAD(P)H as low as $10^{15}$M can be determined by measurement of formation of a NAD(P)H driven product. [B] or [XH$_2$], since the number of cycles per unit time depends on the initial concentration of pyridine nucleotide. Since NAD(P) can be supplied to the cycling reaction by a wide variety of pyridine nucleotide-requiring enzymes, highly sensitive detection can also be achieved for any analyte that is a substrate of an enzyme that can be coupled to a cycling reaction.

Enzymatic cycling reactions can also be used for removal of a toxic substance or unwanted inhibitor from a reaction mixture or biological system. They can be coupled to a wide range of discrete enzymes or multienzyme reaction sequences to catalytically degrade a particular undesirable substance. Multienzyme systems simulating hepatic detoxification processes and renal denitrification reactions, for example, represent enabling tools for valuable biomedical devices. Possible applications include extracorporeal devices for patients with severe hepatic disease; enhanced renal dialysis through enzymatic removal of urea and other toxic metabolites; and in vivo detoxification through multienzyme drugs, implantable devices and artificial organs.

The same principles applicable to nucleotide-directed multienzyme assemblies can also be applied to development of labeling reagents for specific binding assays. Such labeling reagents can amplify a signal to improve the detection limit of a diagnostic assay or transduce a detectable signal into a different type of signal that can be measured using an alternative detection system. Examples of this transduction capability include conversion of: a product that absorbs ultraviolet light into a product that absorbs in the visible range; an electrochemically detectable product into a spectrophotometrically detectable product and vice versa; a spectrophotometrically detectable product into a luminescent or fluorescent product; light of one wavelength into longer wavelength light thereby effectively increasing the Stoke's shift; and a product with a high detection limit into a product with a low detection limit.

Nucleotide-directed molecular assembly provides a practical approach for the juxtaposition of different fluorophores with overlapping emission and absorption spectra. Applications include diagnostics, artificial photosynthesis and optical signal processing. Conjugation of fluorescein, Texas red, rhodamine, phycobiliproteins and other fluorophores to ligands and receptors provides a useful means to quantify specific binding reactions either directly or through fluorescence energy transfer. Application of fluorescence energy transfer to the development of self-organizing molecular photonic structures (Heller et al., *Clinical Chemistry*, 39:742 (1993)) and artificial photosynthesis has also been proposed.

Those skilled in the art will recognize that the general principles of nucleotide-directed enzyme channeling and fluorescence energy transfer can be applied to the interconversion of chemical, electromagnetic, mechanical and thermal energy. Contractile, secretory and transport proteins, for example, represent suitable mechanical acceptors for chemical energy in the same way that cytochromes and chlorophyll serve as acceptors of electrons and photons, respectively, in oxidative metabolism and photosynthesis.

The potential utility of synthetic heteropolymers, multivalent heteropolymeric hybrid structures and multimolecular complexes encompasses all applications for which the ordered arrangement of molecules enables or improves reactions and processes that do not proceed efficiently when such molecules are either randomly distributed or ordered in bulk. Other utilities for the present invention will become obvious to those skilled in the art from this disclosure.

The following examples illustrate certain aspects of the present invention and are not intended to limit the same.

EXAMPLES

Example 1: Homogeneous nucleic acid probe diagnostic employing a multimolecular complex with bound G6PDH to monitor hybridization reactions A first defined sequence segment, approximately 5 to 40 nucleotides, capable of specifically binding glucose-6-phosphate dehydrogenase (G6PDH) so that its enzymatic activity is inhibited, is selected. A second defined sequence segment, a probe sequence, approximately 10 to 20 nucleotides, that is complementary to a defined sequence of an infectious agent, an oncogene or a known genetic defect is also selected. Examples of infectious agents include but are not limited to, HIV, HBV, HCV, CMV, HPV, EBV, RSV, Chlamydia, Gonococcus, and TB. Examples of oncogenes include, but are not limited to, p53 and DCC genes, c-neu, c-myc, N-myc and activated ras oncogenes. Examples of known genetic defects include, but are not limited to, those associated with cystic fibrosis, sickle cell disease, β-thalassemia, Fragile X, Down's syndrome, muscular dystrophy, familial hypercholesterolemia, phenylketonuria, galactosemia, biotinidase deficiency and markers of polygenic disorders. A third nucleotide sequence, capable of linking the first defined sequence which binds G6PDH and the second defined sequence capable of hybridization at a distance sufficient to maintain independent operation of each defined sequence segment is then selected. A heteropolymer is synthesized comprising the first selected defined sequence segment and the second selected defined sequence segment connected by the third nucleotide sequence. G6PDH is then bound to the first defined sequence segment to form a multimolecular complex. About 1 to 50 μl of a sample containing extracted, denatured genomic or plasmid DNA is added to a reaction mixture containing this multimolecular complex, glucose-6-phosphate, nicotinamide adenine dinucleotide phosphate (NAD(P)), sodium azide and phosphate buffered saline. Hybridization of the DNA in the sample to the second defined sequence segment results in a decrease in the affinity of the first defined sequence segment for the G6PDH so that it is no longer bound. The unbound G6PDH, now active, produces reduced NAD(P) (NAD(P)H)

from the NAD(P) in the reaction mixture. This production can be monitored spectrophotometrically at 340 nm or colorimetrically using an indicator such as asiodonitrotetrazolium.

Example 2: High sensitivity homogeneous assays for low molecular weight analytes Detection of the small molecular weight analyte thyroxine ($T_4$) can be accomplished through use of a synthetic heteropolymer whose first defined sequence segment is specific for G6PDH and whose second defined sequence segment is specific for $T_4$. A multimolecular complex is formed by specifically binding G6PDH to the first defined sequence segment and a ligand-carrier conjugate to the second defined sequence segment. Suitable ligands include analogs of $T_4$, particularly iodothyronines such as $T_3$. suitable carriers include non-physiological macromolecules such as non-human proteins and high molecular weight dextrans. In general, the ligand-carrier conjugate is selected on the basis of: its ability to bind the second defined sequence segment of the multimolecular complex with adequate affinity to maintain a stable, quasi-reversible complex; its affinity for the second defined sequence segment being lower than that of native analyte, such that analyte will competitively displace the conjugate; and the degree of inhibition, upon binding, of the signal-generating enzyme specifically bound to the first defined sequence segment of the multimolecular complex. Inhibition may result either from steric hindrance by the bulky carrier group or modulation of the affinity of the first defined sequence segment for the enzyme. Examples of carriers include, but are not limited to, large proteins such as ferritin, Keyhole limpet hemocyanin (KLH), or thyroglobulin, or insoluble particles such as latex microspheres to which ligands are covalently attached through an appropriate spacer such as 5-aminocaproic acid, diaminohexane or various N-hydroxysuccinimide, hydrazide or maleimide derivatives. In this manner, the specifically bound signal-generating enzyme is inactivated when the carrier-ligand conjugate is specifically bound to the analyte recognition sequence of the bifunctional oligonucleotide. When the multimolecular complex is exposed to sample analyte ($T_4$), the ligand-carrier conjugate is displaced by higher affinity analyte and the signal generating enzyme is activated with release of the conjugate.

For detection of $T_4$, a synthetic heteropolymer is synthesized which has a first defined sequence segment capable of specifically binding G6PDH and a second defined sequence segment capable of specifically binding $T_4$. G6PDH is bound to the first defined sequence. A ligand-carrier comprising $T_3$ and KLH is bound to the second defined sequence segment. This multimolecular complex is then used to detect $T_4$ concentrations. About 1 to 50 µl of blood serum or plasma is added to a reaction mixture or dry-reagent device such as a slide, cartridge or sensor containing the multimolecular complex, glucose-6-phosphate, NAD(P) and buffer ingredients. $T_4$ in the sample, which has a higher affinity for the second defined sequence segment than the conjugate binds to the multimolecular complex and displaces $T_3$-KLH conjugate. This displacement results in activation of G6PDH which reduces NAD(P). Thus, concentrations of T4 can be determined by monitoring production of NAD(P)H spectrophotometrically at 340 nm or colorimetrically using an indicator such as asiodonitrotetrazolium.

Example 3: Homogeneous nucleic acid probe diagnostic employing synthetic heteropolymer with bound flavin adenine dinucleotide to monitor hybridization reactions A defined sequence segment of nucleotides, approximately 5 to 20 nucleotides, is selected which is capable of specifically binding flavin adenine dinucleotide (FAD), the prosthetic group for apoglucose oxidase, in such a manner that the FAD is inaccessible to apoglucose oxidase. Apoglucose oxidase is inactive until reconstituted to the holoenzyme glucose oxidase with FAD. A second defined sequence segment of approximately 10 to 20 nucleotides that is complementary to a defined sequence of an infectious agent, an oncogene or a known genetic defect is selected as a probe. Examples of infectious agents include, but are not limited to, HIV, HBV, HCV, CMV, HPV, EBV, RSV, Chlamydia, Gonococci, and TB. Examples of oncogenes include, but are not limited to, p53 and DCC genes, c-neu, c-myc, N-myc and activated ras oncogenes. Examples of known genetic defects include, but are not limited to, those associated with, cystic fibrosis, sickle cell disease, β-thalassemia, Fragile X, Down's syndrome, muscular dystrophy, familial hypercholesterolemia, phenylketonuria, galactosemia, biotinidase deficiency and markers of polygenic disorders. A third nucleotide sequence is selected which is capable of linking the first selected sequence and the second selected sequence in such a manner that each sequence remains independently operative. A heteropolymer is synthesized which contains the first and second selected defined sequence segments linked by the third nucleotide sequence. FAD is then bound to the first defined sequence segment of the heteropolymer to form a multimolecular complex. About 1 to 50 µl of a sample containing extracted, denatured genomic or plasmid DNA is added to a reaction mixture containing this multimolecular complex, apoglucose oxidase, glucose, horseradish peroxidase, and buffer. Hybridization of DNA in the sample to the second defined sequence segment alters the affinity of the first defined sequence segment for the FAD such that bound FAD is displaced or rendered sterically accessible to apoglucose oxidase. Glucose oxidase is thereby reconstituted in proportion to the number of hybridization events, so the concentration of target sequences can be quantified either photometrically through coupling of glucose oxidase to a chromogenic peroxidase reaction or electrochemically through coupling to an amperometric enzyme electrode. Enzymatic oxidation of 2,2'-azino-bis(3-ethylbenzthiazoline-6-sulfonic acid (ABTS) by peroxidase is monitored spectrophotometrically at 405 nm and the concentration of target nucleic acid is determined as the rate of change of absorbance compared with rates for calibrator solutions. Alternatively, reactions can be stopped at a fixed time point, approximately 10 to 60 minutes, by addition of 1% sodium dodecyl sulfate for endpoint measurements.

Example 4: Enzyme channeling reagents for coupled-enzyme clinical chemistry assays Clinical chemistry analytes can be measured with high efficiency and sensitivity using enzyme channeling complexes assembled from selected enzymes specifically bound to synthetic heteropolymers or multivalent heteropolymeric hybrid structures. In this embodiment, the analyte of interest must be a substrate of a first selected enzyme. One or more additional enzyme reactions are coupled to the first enzyme reaction to yield a detectable signal, preferably an amplified detectable signal. The selection of coupling enzymes is based on the preferred detection method. For example, different enzymes or enzyme combinations are preferred for electrochemical versus optical measurements, ultraviolet versus visible absorbance measurements, and rate versus endpoint measurements.

All of the examples that follow can be practiced with multimolecular complexes comprising two or more enzymes specifically bound to either a synthetic heteropolymer or a multivalent heteropolymeric hybrid structure. Multivalent heteropolymeric hybrid structures are preferred, because they allow convenient evaluation and optimization of different specifically bound enzyme combinations using a library of defined sequence segments that specifically bind different enzymes.

Multimolecular complexes for each combination of enzymes are prepared from multivalent heteropolymeric hybrid structures as follows. For two-enzyme complexes, two synthetic heteropolymers are synthesized, each having a selected first defined sequence segment capable of specifically binding a selected enzyme and a second defined sequence segment capable of hybridizing. The first defined sequence segments are selected for maximal enzyme-binding affinity and minimal inhibition of enzyme activity. The second defined sequence segments are complementary, capable of hybridizing the two synthetic heteropolymers into a multivalent heteropolymeric hybrid structure. The selected enzymes are then specifically bound to their respective defined sequence segments to form multimolecular complexes. For three-enzyme complexes, two sequence segments capable of hybridizing are selected for the third synthetic heteropolymer, each capable of hybridizing to a second defined sequence segment of another synthetic heteropolymer of the multivalent heteropolymeric hybrid structure. The synthetic heteropolymers are then hybridized, and the selected enzymes are specifically bound to their respective sequence segments to form a multimolecular complex. A four-enzyme system may be assembled in a similar manner by preparing two synthetic heteropolymers, each having one hybridizing sequence segment, and two synthetic heteropolymers, each having two hybridizing sequence segments. Alternatively, a four-enzyme system may be developed using a pair of two-enzyme complexes, as exemplified by triglyceride detection in the instant example.

Examples of coupled enzyme reactions for detection of clinical chemistry analytes using multimolecular complexes are provided below.

Detection of cholesterol:

Cholesterol is a serum lipid and a constituent of lipoproteins. Increased serum levels may occur in atherosclerosis, nephrosis, diabetes mellitus, myxedema and obstructive jaundice. Decreased levels have been observed in hyperthyroidism, certain anemias, malabsorption and wasting syndromes.

The coupled enzymatic reactions are as follows: cholesterol ester plus water in the presence of cholesterol esterase yields cholesterol plus fatty acids; cholesterol plus oxygen in the presence of cholesterol oxidase yields cholest-4-en-3-one plus hydrogen peroxide; hydrogen peroxide plus 4-aminoantipyrine plus p-sulfonatehydroxybenzene in the presence of peroxidase yields quinoneimine dye plus water.

A multimolecular complex comprising cholesterol esterase and cholesterol oxidase specifically bound to a multivalent heteropolymeric hybrid structure is assembled. Cholesterol levels in a sample can then be measured through amperometric detection of the consumption of oxygen or the production of peroxide. Alternatively, cholesterol can be measured photometrically by using all three enzymes coupled through a trifunctional multivalent heteropolymeric hybrid structure and detecting the oxidized quinoneimine dye at 500 nm.

Detection of triglycerides:

Triglycerides represent the predominant form of fatty acids in blood. Serum levels are used to classify various types of hyperlipoproteinemia. Serum triglyceride levels may be elevated in nephrotic syndrome, coronary artery disease, hypothyroidism, diabetes mellitus and liver disease. Decreased levels may be observed in protein malnutrition, hyperthyroidism, cachectic states and abetalipoproteinemia.

The coupled enzymatic reactions are as follows: triglycerides in the presence of lipoprotein lipase yields glycerol plus fatty acids; glycerol plus ATP in the presence of glycerol kinase yields glycerol-1-phosphate plus ADP; glycerol-1-phosphate plus oxygen in the presence of glycerol phosphate oxidase yields dihydroacetone phosphate plus peroxide; peroxide plus 4-aminoantipyrine plus N-ethyl-N-(3-sulfopropyl)m-anisidine in the presence of peroxidase yields quinoneimine dye plus water.

Using a three enzyme multimolecular complex, triglycerides are measured through amperometric determination of glycerol phosphate oxidase activity either as oxygen consumption or peroxide production. Using all four of the above enzymes in paired, two-enzyme multimolecular complexes, triglycerides are measured photometrically through detection of quinoneimine dye absorbance at 540 nm.

Detection of creatine kinase:

Creatine kinase is a cardiac, brain and muscle enzyme whose serum levels increase four to six hours following myocardial infarction and peak after 18–30 hours. Elevated levels are also associated with muscular dystrophy, hypothyroidism, pulmonary infarction and acute cerebrovascular disease.

The coupled enzymatic reactions are as follows: ADP plus creatinine phosphate in the presence of creatinine kinase yields creatinine plus ATP; ATP plus glucose in the presence of hexokinase yields ADP plus glucose-6-phosphate; glucose-6-phosphate plus NAD in the presence of glucose-6-phosphate dehydrogenase yields 6-phosphogluconate plus NADH.

Using a three enzyme multimolecular complex, creatine kinase activity is detected spectrophotometrically as the increase in NADH absorbance at 340 nm or electrochemically through amperometric determination of NAD reduction using a modified G6PDH electrode.

Detection of alanine aminotransferase:

Alanine aminotransferase (ALT) is a liver enzyme routinely included in clinical chemistry profiles. Increased serum levels are associated with hepatitis and other liver diseases.

The coupled enzymatic reactions are as follows: L-alanine plus 2-oxoglutarate alanine in the presence of aminotransferase yields pyruvate plus L-glutamate; pyruvate plus NADH in the presence of lactate dehydrogenase yields L-lactate and NAD.

Oxidation of NADH can be detected spectrophotometrically at 340 nm or amperometrically using a modified lactate dehydrogenase electrode.

Detection of amylase:

Amylase is a pancreatic enzyme whose serum levels increase in acute pancreatitis, pancreatic duct obstruction, intra-abdominal diseases, mumps and bacterial parotitis.

The coupled enzymatic reactions are as follows: p-nitrophenyl-a-D-maltoheptaoside (PNPG7) in the presence of a-amylase yields p-nitrophenylmaltotriose (PNPG3) plus maltotetraose; PNPG3 in the presence of glucoamylase yields p-nitrophenylglycoside (PNPG1) plus glucose; PNPG1 in the presence of a-glucosidase yields nitrophenol plus glucose.

Amylase is detected through photometric detection of p-nitrophenyl at 405 nm.

Detection of aspartate aminotransferase:

Aspartate aminotransferase is a muscle and liver enzyme whose serum levels increase with myocardial infarction, liver cell damage, muscular dystrophy and dermatomyositis.

The coupled enzymatic reactions are as follows: L-aspartate plus 2-oxoglutarate in the presence of aspartate aminotransferase yields oxalacetate plus L-glutamate; oxalacetate plus NADH in the presence of malate dehydrogenase yields L-malate and NAD.

Aspartate aminotransferase activity is measured kinetically through photometric detection of NADH at 340 nm or amperometric detection of NADH oxidation using a modified malate dehydrogenase electrode.

Detection of urea:

Urea nitrogen levels in blood are used as an index of protein catabolism. Increased levels are observed in renal disease, dehydration, diabetic coma, hypoadrenal crisis, gastrointestinal hemorrhage and circulatory collapse. Decreased levels are sometimes seen in severe liver disease.

The coupled enzymatic reactions are as follows: urea plus water in the presence of urease yields carbon dioxide and ammonia; ammonia plus 2-oxoglutarate plus NADH in the presence of glutamate dehydrogenase yields glutamate plus NAD plus water.

Urea levels are quantified photometrically by measuring the decrease in NADH absorbance at 340 nm or amperometrically by measuring oxidation of NADH using a modified glutamate dehydrogenase electrode.

Detection of uric acid:

Uric acid is an end-product of nitrogen metabolism. Increased serum levels occur in gout, leukemia, toxemia of pregnancy and severe renal impairment.

The coupled enzyme reactions are as follows: uric acid plus water plus oxygen in the presence of uricase yields allantoin plus carbon dioxide plus hydrogen peroxide; hydrogen peroxide plus 3,5-dichloro-2-hydroxybenzenesulfonate plus 4-aminoantipyrine in the presence of peroxidase yields quinoneimine dye plus water.

Uric acid is measured through photometric detection of oxidized quinoneimine dye at 520 nm.

Detection of phosphohexose isomerase:

Phosphohexose isomerase is a cellular enzyme that plays an important role in carbohydrate metabolism. Increased serum levels are associated with various types of carcinoma, and levels appear to correlate with the stage of the neoplastic process.

The coupled enzyme reactions are as follows: fructose-6-phosphate in the presence of phosphohexose isomerase yields glucose-6-phosphate; and glucose-6-phosphate plus NAD(P) in the presence of glucose-6-phosphate dehydrogenase yields 6-phosphogluconate plus NAD(P)H.

Phosphohexose isomerase is measured through photometric detection of NAD(P)H at 340 nm or through amperometric detection of the reduction of NAD(P) using a modified G-GPDH electrode.

Detection of carbon dioxide:

Carbon dioxide is a blood gas whose measurement is useful in the assessment of acid-base imbalances. Increases are associated with metabolic alkalosis and respiratory acidosis. Decreases occur in metabolic acidosis and respiratory alkalosis.

The coupled enzymatic reactions are as follows: phosphoenol pyruvate plus carbonate in the presence of phosphoenol pyruvate carboxylase yields oxalacetate plus hydrogen phosphate; oxalacetate plus NADH in the presence of maleate dehydrogenase yields L-malate plus NAD. Carbon dioxide can be measured through photometric detection of NADH at 340 nm or amperometric detection of NADH oxidation using a suitable electron transfer mediator.

Detection of glucose:

Glucose is a blood sugar whose levels are elevated in diabetes mellitus and hyperactivity of the thyroid, pituitary or adrenal glands. Decreased blood glucose levels occur with insulin overdose, insulin-secreting tumors, myxedema, hypopituitarism, hypoadrenalism and glucose malabsorption.

The coupled enzymatic reactions are as follows: glucose plus water plus oxygen in the presence of glucose oxidase yields gluconic acid plus hydrogen peroxide; hydrogen peroxide plus 4-aminoantipyrine plus p-hydroxybenzene sulfonate in the presence of peroxidase yields quinoneimine dye plus water.

Glucose is detected colorimetrically through detection of the oxidized quinoneimine dye at 505 nm.

Example 5: Enzyme channeling complex

Enzyme channeling complexes can be applied to any amplified specific binding assay, including pseudo-immunodiagnostics, DNA probe assays, receptor-based assays and bioaffinity sensors and to biosynthesis, bioprocessing, computer-aided metabolic simulation and detoxification.

Similar multimolecular complexes are also useful in energy transfer reactions including, but not limited to, fluorescent, phosphorescent, chemiluminescent and bioluminescent energy transfer reactions. A simple channeling complex in which a product ($P_1$) of a donor enzyme ($E_1$) is a substrate, coenzyme or prosthetic group for an acceptor enzyme ($E_2$) is prepared from a synthetic heteropolymer comprising a nucleotide sequence having a first defined sequence segment capable of specifically binding $E_1$ and a second defined sequence segment capable of specifically binding $E_2$. It is preferred that the product channeled from donor to acceptor enzyme is a coenzyme or prosthetic group of the acceptor enzyme, rather than a substrate, so that each channeled product catalytically activates the acceptor enzyme. The length and composition of the spacer sequence of the synthetic heteropolymer are optimized to ensure intimate proximity between the donor enzyme and the acceptor enzyme. Examples of preferred effector combinations and their corresponding substrates are provided in the following table.

| Coupled effectors (E1, E2) | Substrates | Products (P1, P2) |
|---|---|---|
| Enzyme channeling | | |
| E1: glucose oxidase | glucose | P1: peroxide |
| E2: peroxidase | reduce indicator | P2: oxidized indicator (color) |
| Enzyme channeling | | |
| E1: hexokinase | ATP, glucose | P1: glucose-6-P |
| E2: G-6-P dehydrogenase | NAD | P2: gluconolactone-6-P, NADH (ultraviolet absorbance) |

-continued

| Coupled effectors (E1, E2) | Substrates | Products (P1, P2) |
|---|---|---|
| *Allosteric activation* | | |
| E1: phosphofructokinase<br>E2: phosphoenol pyruvate carboxylase | fructose-6-phosphate<br>NADH<br>(malate dehydrogenase) | P1: phosphoenol pyruvate<br>P2: $NAD^+$ (enhanced signal via allosteric activation) |
| *Enzyme-driven bioluminescence* | | |
| E1: NAD oxidoreductase<br>E2: luciferase | NADH<br>FMN | P1: $FMNH_2$<br>P2: photons (bioluminescence) |
| *Enzyme-driven chemiluminescence* | | |
| E1: peroxidase<br>E2: luminol | peroxide | P1: $H_2O$<br>P2: photons (chemiluminescence) |
| *Fluorescent energy transfer* | | |
| E1: fluorescein | absorption at 488 nm | P1: emission at 525 nm |
| E2: B-phycoerythrin | absorption at 525 nm | P2: emission at 576 nm |
| *Fluorescent energy transfer* | | |
| E1: B-phycoerythrin | absorption at 495 nm | P1: emission at 576 nm |
| E2: R-phycocyanin | absorption at 576 nm | P2: emission at 642 nm |
| *Fluorescent energy transfer* | | |
| E1: R-phycocyanin | absorption at 555 nm | P1: emission at 642 nm |
| E2: allophycocyanin | absorption at 642 nm | P2: emission at 660 nm |

Alternatively, enzymes that interact through allosteric inhibition can be coupled in an inhibited state in multimolecular complexes such that inhibition is disrupted by analyte binding to a defined sequence segment, yielding homogenous enzyme activation. Aspartate aminotransferase and phosphoenol pyruvate carboxylase, for example, can be used in homogeneous specific binding assays relying on analyte-dependent disruption of negative cooperativity.

Any of the above-listed combinations of molecular effectors can be brought into close spatial proximity for use as signal-generating diagnostic reagents through nucleotide-directed assembly. The spatial arrangement of specific binding sequences within a given multivalent heteropolymeric hybrid structure must be optimized for a given pair or group of molecular effectors to achieve the desired efficiency of channeling or energy transfer.

Spatial optimization is accomplished through systematic production and evaluation of synthetic heteropolymers with varying spacer sequences and of multivalent heteropolymeric hybrid structures with varying hybridized sequence segments and linker oligonucleotides.

Preparation of multimolecular fluorescence energy transfer complexes comprising synthetic heteropolymers The phycobiliprotein B-phycoerythrin, isolated from red algae, is an excellent energy acceptor when fluorescein is used as donor. The efficiency of Forster energy transfer from fluorescein to B-phycoerythrin approaches 100% as the distance between fluorescein and the surface of the phycoerythrin protein decreases to approximately 2 nm. 50% efficiency occurs at about 8.7 nm and significant energy transfer (>20% efficiency) occurs at distances up to about 11 nm.

Double-stranded DNA has a periodicity of approximately 0.34 nm (3.4Å), equivalent to 10 nucleotide base pairs per 3.4 nm. When fluorescein and phycoerythrin are specifically bound at defined sequence segments separated by hybridized sequences in a multimolecular complex, the efficiency of energy transfer from fluorescein to phycoerythrin depends on the length of defined sequence segments separating the bound fluorophores. Since the diameter of phycoerythrin is approximately 3 nm to 6 nm, a multivalent heteropolymeric hybrid comprising a fluorescein-binding heteropolymer hybridized to a phycoerythrin-binding heteropolymer will position fluorescein and phycoerythrin for efficient energy transfer provided they are separated by less than about 40 base pairs. Maximally efficient energy transfer occurs if binding sequences are separated by linker sequences less than or equal to about 10 base pairs in length.

Preparation of fluorescence energy transfer complexes using multivalent heteropolymeric hybrid structures to assemble selected fluorophores The following reagents were used. Fluorescein conjugate: fluorescein ($C_{20}H_{12}O_5$; FW=332.3; available as free acid, sodium salt and derivatives) may be conjugated to a wide range of carriers, including proteins, peptides, oligosaccharides, oligonucleotides and low molecular weight haptens. Preferred derivatives for conjugation include fluorescein isothiocyanate (FITC) and fluorescein succinimidyl esters. For convenience, commercially available FITC-dextran (average MW=40,000; specific activity= 0.003–0.020 mole FITC per mole glucose) was selected for this example.

B-phycoerythrin (MW=240,000; isolated from red alga *Porphyridium cruentum*)

B-phycocyanin (MW=110,000; isolated from red alga *Porphyridium cruentum*)

Allophycocyanin (MW=104,000; isolated from filamentous cyanobacterium *Anabaena variabilis*)

Multivalent heteropolymeric hybrid structures are prepared by self-assembly of two or more fluorophore-binding synthetic heteropolymers, each having three defined sequence segments as follows:

| Fluorophore Specificity | Defined sequence segments |
|---|---|
| FITC-dextran | internal segment specifically binds FITC-dextran; 5' and 3' sequence segments specifically hybridize to complementary sequence segments of other synthetic heteropolymers |
| B-phycoerythrin | internal segment specifically binds B-phycoerythrin; 5' and 3' sequence segments specifically hybridize to complementary sequence segments of other synthetic heteropolymers |
| R-phycocyanin | internal segment specifically binds R-phycocyanin; 5' and 3' sequence segments specifically hybridize to complementary sequence segments of other synthetic heteropolymers |
| Allophycocyanin | internal segment specifically binds allophycocyanin; 5' and 3' sequence segments specifically hybridize to complementary sequence segments of other synthetic heteropolymers |

Different combinations of the above-listed synthetic heteropolymers are mixed in equimolar amounts to yield the following structures useful in assembling energy transfer complexes: three permutations of bivalent heteropolymeric hybrid structures; two permutations of trivalent heteropolymeric hybrid structures; or a single tetravalent heteropolymeric hybrid structure.

Sequential incubation of each preparation with equimolar or greater concentrations of each targeted fluorophore yields the following energy transfer complexes:

| | Idealized Stoke's shift (nm) | | |
|---|---|---|---|
| Nucleotide-ordered fluorophores | Abs | Emax | Δ (E − A) |
| FITC-dextran + phycoerythrin | 490 | 575 | 85 |
| phycoerythrin + phycocyanin | 543 | 642 | 99 |
| phycocyanin + allophycocyanin | 555 | 660 | 105 |
| FITC-dextran + phycoerythrin + phycocyanin | 490 | 642 | 152 |
| phycoerythrin + phycocyanin + allophycocyanin | 543 | 660 | 117 |
| FITC-dextran + phycoerythrin + phycocyanin + allophycocyanin | 490 | 660 | 170 |

Preparation of fluorescence energy transfer complexes with specific binding capabilities Nucleotide-ordered fluorescence energy transfer complexes such as those described above can be hybridized with synthetic heteropolymers comprising a suitable complementary defined sequence segment plus a defined sequence segment selected for specific binding to a ligand or receptor. The resulting multimolecular energy transfer-probe complexes, having both specific binding and fluorescence energy transfer capabilities, can be used as labeled probes in a number of diagnostic applications, such as fluorescence activated cell sorting, immunohistochemical studies and immunodiagnostics. In addition, self-assembling complexes of fluorophores and ligand- or receptor-binding synthetic heteropolymers can be designed to provide for modulation of energy transfer efficiency upon exposure to a particular ligand or receptor. A number nucleotide-directed complexes for ligand- or receptor-modulated energy transfer can be developed, depending on the size and properties of the ligand or receptor, the range of concentrations to be detected and the preferred frequencies of excitation and detection.

In one embodiment, ligand-sensitive energy transfer complexes for high molecular weight and low molecular weight ligands and receptors, hereinafter analytes, are assembled as follows. For high molecular weight analytes, a multivalent heteropolymeric hybrid structure is prepared comprising three defined sequence segments capable of specifically binding non-oligonucleotide molecules. The defined sequence segments at the 5' and 3' ends of the nucleotide structure are selected for high-affinity binding to FITC-dextran and B-phycoerythrin, respectively. The internal defined sequence segment is selected for high-affinity binding to a high molecular weight analyte, such as TSH, hCG, FSH, LH, TGB, CEA, AFP, PSA, CK-MB, an infectious disease antigen, and apolipoprotein, a cancer antigen, a cell surface marker or an immunoglobulin. This hybrid structure is then incubated with FITC-dextran and B-phycoerythrin to yield a multimolecular fluorescence energy transfer complex comprising FITC-dextran and B-phycoerythrin specifically bound to the 5' and 3' ends of the heteropolymeric hybrid structure, separated by an internal analyte-binding sequence. Within this multimolecular complex, FITC-dextran and B-phycoerythrin are separated by a distance of 2–10 nm, spanning the analyte-binding sequence and hybridized defined sequence segments, such that upon exposure to a 488 nm argon-ion laser, fluorescence energy is efficiently transferred from fluorescein to B-phycoerythrin. With subsequent addition of sample containing analyte, specific binding to the analyte-binding sequence between the two fluorophores occludes energy transfer from FITC-dextran to B-phycoerythrin. Specific binding is detected either as a decrease in B-phycoerythrin emission at 575 nm or as an increase in fluorescein emission at 515 nm.

For low molecular weight analytes, an analogous multimolecular complex is prepared comprising 5' and 3' defined sequence segments selected for high-affinity binding to FITC-dextran and R-phycocyanin. The internal defined sequence segment is selected for high-affinity binding to a hapten, such as $T_4$, $T_3$ estriol, estradiol, progesterone, cortisol, a therapeutic drug or a drug of abuse. A conjugate comprising a structural analog of the selected analyte covalently attached to B-phycoerythrin is specifically bound to the internal defined sequence segment of the multimolecular complex through the analog moiety. This defined sequence segment is selected to provide for stable, quasi-reversible binding to the conjugate, but of lower affinity than for the native analyte. For this example, the internal defined sequence segment was selected for high-affinity binding to $T_4$ with lesser affinity for $T_3$-phycoerythrin. In the absence of free ligand, illumination of the multimolecular complex with a 488 nm argon-ion laser results in efficient fluorescence energy transfer from fluorescein ($E_{max}$=515 nm) to B-phycoerythrin ($E_{max}$=575 nm) to R-phycocyanin displaced from the complex, interrupting the transfer of energy from fluorescein to the $T_3$ phycoerythrin conjugate and from the conjugate to R-phycocyanin. Specific binding of $T_4$ is measured either as a decrease in B-phycoerythrin emission at 575 nm, a decrease in R-phycocyanin emission at 642 nm, an increase in fluorescein emission at 525 nm, or some combination of the three measurements.

Example 6: Enzymatic Cycling Complex

An enzymatic cycling complex can also be assembled by the multivalent heteropolymeric hybrid structures described in Example 4, supra. In an enzymatic cycling complex, the product of the acceptor enzyme $E_2$ is also a substrate, coenzyme or prosthetic group for donor enzyme $E_1$. There are many enzyme pairs suitable for this type of cycling reaction, the most prominent being dehydrogenases and oxidoreductases relying on nicotinamide and flavin dinucleotide coenzymes to shuttle electrons.

An example of enzymatic cycling using two pyridine nucleotide-dependent enzymes is illustrated below.

In this example, conversion of a first substrate to product by a first enzyme ($E_a$) is linked to reduction of a second substrate by a second enzyme ($E_x$) through the pyridine nucleotide NAD(P). The oxidized coenzyme NAD(P) is reduced by $E_a$ to NAD(P)H which is required as a coenzyme for the reduction of the second substrate by $E_x$.

Such complexes may be amplified by having the donor enzyme $E_1$ channel two or more molecules of product per cycle to the acceptor enzyme $E_2$ which, in turn, channels two or more product molecules to donor enzyme $E_1$. This complex provides a means to achieve exponential increases in the rate of product formation, enabling development of high sensitivity detection systems for diagnostic tests. An example of suitable paired enzymes for such a complex is the combination of myokinase and pyruvate kinase to convert one molecule each of ATP and AMP to four molecules of ATP per cycle. An example of this cycling is illustrated below for two pyridine nucleotide requiring enzymes.

What is claimed:

1. A synthetic heteropolymer comprising a single stranded nucleic acid molecule having at least a first and a second defined sequence segment, wherein the first defined sequence segment is capable of specifically and noncovalently binding to a first non-oligonucleotide molecule having a selected activity and the second defined sequence segment is capable of specifically and noncovalently binding to a second, different non-oligonucleotide molecule having a selected activity, wherein said first and second defined sequence segments are not known to be biological recognition sites for said first and second nonoligonucleotide molecules.

2. A synthetic heteropolymer comprising a single stranded nucleic acid molecule having at least a first and a second defined sequence segment, wherein the first defined sequence segment is not known to be a biological recognition site for nonoligonucleotide molecules and is capable of specifically and noncovalently binding to a non-oligonucleotide molecule having a selected activity and the second defined sequence segment is capable of hybridization to a selected nucleic acid sequence which does not hybridize to said first defined sequence segment, said first and second defined sequence segments bringing said nonoligonucleotide molecule and said nucleic acid sequence into proximity such that the binding or activity of said nonoligonucleotide molecule is modulated by binding of the selected nucleic acid sequence.

3. A multimolecular complex comprising a synthetic heteropolymer of claim 2 having a non-oligonucleotide molecule specifically bound to the first defined sequence segment of said heteropolymer.

4. The multimolecular complex of claim 3 wherein a selected activity of the non-oligonucleotide molecule specifically bound to the first defined sequence segment is modulated by hybridization of the second defined sequence segment of said heteropolymer.

5. The multimolecular complex of claim 3 wherein the affinity of the first defined sequence segment for the bound non-oligonucleotide molecule is modulated by hybridization of the second defined sequence segment of said heteropolymer.

6. A multivalent heteropolymeric hybrid structure comprising at least two synthetic heteropolymers, each synthetic heteropolymer being a single stranded nucleic acid molecule comprising at least a first and a second defined sequence segment, wherein said first defined sequence segment is not known to be a biological recognition site for nonoligonucleotide molecules and is capable of specifically and noncovalently binding to a non-oligonucleotide molecule and the second defined sequence segment being capable of hybridization.

7. The multivalent heteropolymeric hybrid structure of claim 6 wherein the second defined sequence segment of each synthetic heteropolymer comprises 5 to 40 nucleotides.

8. The multivalent heteropolymeric hybrid structure of claim 6 comprising two synthetic heteropolymers, each synthetic heteropolymer having a second defined sequence segment capable of hybridizing the two synthetic heteropolymers.

9. The multivalent heteropolymeric hybrid structure of claim 6 further comprising a linker oligonucleotide capable of hybridizing to the second defined sequence segment of each synthetic heteropolymer and joining the synthetic heteropolymers.

10. The multivalent heteropolymeric hybrid structure of claim 9 wherein the linker oligonucleotide comprises a duplex structure having single-stranded ends capable of hybridizing to the second defined sequence segments of the synthetic heteropolymers.

11. The multivalent heteropolymeric hybrid structure of claim 9 wherein the linker oligonucleotide comprises a triplex structure capable of hybridizing to the second defined sequence segments of the synthetic heteropolymers.

12. The multivalent heteropolymeric hybrid structure of claim 9 wherein the linker oligonucleotide comprises a branched-chain structure having defined sequence segments capable of hybridizing to the second defined sequence segments of the synthetic heteropolymers.

13. The multivalent heteropolymeric hybrid structure of claim 9 wherein the linker oligonucleotide comprises a circular structure having defined sequence segments capable of hybridizing to the second defined sequence segment of each synthetic heteropolymer.

14. A multimolecular complex comprising a multivalent heteropolymeric hybrid structure of claim 6 having a first non-oligonucleotide molecule specifically bound to the first defined sequence segment of the first synthetic heteropolymer of said heteropolymeric hybrid structure.

15. The multimolecular complex of claim 14 wherein the specific binding of the first non-oligonucleotide molecule to the first defined sequence segment of the first synthetic heteropolymer of said heteropolymeric hybrid structure modulates the affinity of the first defined sequence segment of a second synthetic heteropolymer of said heteropolymeric hybrid structure for a second non-oligonucleotide molecule.

16. The multimolecular complex of claim 14 wherein the specific binding of the first non-oligonucleotide molecule to the first defined sequence segment of the first synthetic heteropolymer of said heteropolymeric hybrid structure modulates a selected activity of a second, different non-oligonucleotide molecule specifically bound to the first defined sequence segment of the second synthetic heteropolymer of said heteropolymeric hybrid structure.

17. The multimolecular complex of claim 14 further comprising a second non-oligonucleotide molecule having a selected activity specifically bound to the first defined sequence segment of the second synthetic heteropolymer of said heteropolymeric hybrid structure.

18. A multivalent heteropolymeric hybrid structure comprising a first synthetic heteropolymer which is a single stranded nucleic acid molecule having at least a first and second defined sequence segment, wherein the first defined sequence segment is not known to be a biological recognition site for nonoligonucleotide molecules and is capable of specifically and noncovalently binding to a non-oligonucleotide molecule having a selected activity and wherein the second defined sequence segment is capable of hybridization, and a second synthetic heteropolymer which is a single stranded nucleic acid molecule having at least two defined sequence segments capable of hybridization.

19. A multimolecular complex comprising a synthetic heteropolymer of claim 1 having a first non-oligonucleotide molecule specifically bound to the first defined sequence segment of said heteropolymer.

20. The multimolecular complex of claim 19 wherein the specific binding of the first non-oligonucleotide molecule to the first defined sequence segment modulates the affinity of the second defined sequence segment of said heteropolymer for a second, different non-oligonucleotide molecule.

21. The multimolecular complex of claim 19 wherein the specific binding of the first non-oligonucleotide molecule to the first defined sequence segment modulates a selected activity of a second, different non-oligonucleotide molecule specifically bound to the second defined sequence segment of said heteropolymer.

22. The multimolecular complex of claim 19 further comprising a second non-oligonucleotide molecule specifically bound to the second defined sequence segment of said heteropolymer.

* * * * *